(12) United States Patent
Ogawa et al.

(10) Patent No.: US 8,450,462 B2
(45) Date of Patent: May 28, 2013

(54) COMPOUND

(75) Inventors: Satoshi Ogawa, Tokyo (JP); Fumio Yamauchi, Yokohama (JP); Kengo Kanazaki, Yokohama (JP); Mayuko Kishi, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 7 days.

(21) Appl. No.: 12/821,711

(22) Filed: Jun. 23, 2010

(65) Prior Publication Data

US 2011/0064666 A1 Mar. 17, 2011

(30) Foreign Application Priority Data

Jun. 26, 2009 (JP) ................................. 2009-152611
May 11, 2010 (JP) ................................. 2010-109288

(51) Int. Cl.
*C07K 16/28* (2006.01)
*C07K 16/46* (2006.01)
*A61K 49/06* (2006.01)
*A61K 49/16* (2006.01)
*A61K 49/22* (2006.01)

(52) U.S. Cl.
USPC ... 530/387.3; 530/391.3; 424/9.1; 424/185.1; 424/192.1; 424/193.1

(58) Field of Classification Search
None
See application file for complete search history.

(56) References Cited

U.S. PATENT DOCUMENTS

| 5,621,083 | A | 4/1997 | Better | |
|---|---|---|---|---|
| 7,169,892 | B2 * | 1/2007 | Atsushi et al. | 530/328 |
| 7,368,254 | B2 * | 5/2008 | Jorgensen et al. | 435/7.23 |
| 2004/0259768 | A1* | 12/2004 | Lauermann | 514/2 |

FOREIGN PATENT DOCUMENTS

| JP | 2000-507577 T | | 6/2000 |
|---|---|---|---|
| JP | 2008-245616 A | | 10/2008 |
| WO | WO 2008073851 | * | 6/2008 |
| WO | WO 2008119566 | * | 10/2008 |

OTHER PUBLICATIONS

Stryer et al, in Biochemistry, Third edition, W H Freeman Company, New York, pp. 31-33, 1998.*
Ngo et al., The Protein Folding Problem and Tertiary Structure Prediction, pp. 492-495, 1994.*
Yu et al, Investigative Ophthalmology & Visual Science 49(2): 522-527, Feb. 2008.*
Witte et al, Cancer and Metastasis Reviews 17: 155-161, 1998.*
Cochran et al., J. Immunol. Meth. 287: 147-158, 2004.*
Rehault et al, Biochimica et Biophysica Acta 1596: 55-62, 2002.*
Yang et al, Protein Engineering 16: 761-770, 2003.*
Kubetzko, Susanne, P"PEGylation and Multimerization of the Anti-p185HER-2 Single Chain FvFragment 4D5", Journal of Biological Chemistry, 281, 35186-35201(Nov. 17, 2006).

* cited by examiner

*Primary Examiner* — Phuong Huynh
(74) *Attorney, Agent, or Firm* — Canon U.S.A., Inc., IP Division

(57) ABSTRACT

A compound including a polymer is represented by general formula (1):

$$L\text{-}Y\text{-}A \qquad (1)$$

wherein, A is a single-chain antibody moiety, which is a polypeptide including an antigen-binding site, L is a linker moiety, which is a polypeptide including a protease cleavage site, Y is a peptide moiety, which includes 0 or more amino acids connecting the linker moiety L with the single-chain antibody moiety A, and the linker moiety L binds to an N terminus of the peptide moiety Y or an N terminus of the single-chain antibody moiety A.

9 Claims, 5 Drawing Sheets

SEQUENCE LISTING

```
<160> NUMBER OF SEQ ID NOS: 8

<210> SEQ ID NO 1
<211> LENGTH: 242
<212> TYPE: PRT
<213> ORGANISM: Artificial Sequence
<220> FEATURE:
<223> OTHER INFORMATION: sdFv region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
                180                 185                 190

Ser Ala Asp Thr Ser Lys Asn Thr Ala Tyr Leu Gln Met Asn Ser Leu
                195                 200                 205

Arg Ala Glu Asp Thr Ala Val Tyr Tyr Cys Ser Arg Trp Gly Gly Asp
210                 215                 220

Gly Phe Tyr Ala Met Asp Tyr Trp Gly Gln Gly Thr Leu Val Thr Val
225                 230                 235                 240

Ser Ser

<210> SEQ ID NO 2
<211> LENGTH: 5
<212> TYPE: PRT
<213> ORGANISM: Artificial Sequence
<220> FEATURE:
<223> OTHER INFORMATION: cleavage region

<400> SEQUENCE: 2

Pro Leu Gly Val Arg
1               5

<210> SEQ ID NO 3
<211> LENGTH: 10
<212> TYPE: PRT
<213> ORGANISM: Artificial Sequence
<220> FEATURE:
<223> OTHER INFORMATION: scFv region

<400> SEQUENCE: 3

Ser Ser Ile Tyr Ser Gln Thr Glu Glu Gln
1               5                   10

<210> SEQ ID NO 4
<211> LENGTH: 267
<212> TYPE: PRT
<213> ORGANISM: Artificial Sequence
<220> FEATURE:
<223> OTHER INFORMATION: scFv-NM

<400> SEQUENCE: 4

Met Ser Gly Pro Leu Gly Val Arg Gly Ala Met Asp Ile Gln Met Thr
1               5                   10                  15

Gln Ser Pro Ser Ser Leu Ser Ala Ser Val Gly Asp Arg Val Thr Ile
                20                  25                  30
```

```
Thr Cys Arg Ala Ser Gln Asp Val Asn Thr Ala Val Ala Trp Tyr Gln
            35                  40                  45

Gln Lys Pro Gly Lys Ala Pro Lys Leu Leu Ile Tyr Ser Ala Ser Phe
 50                  55                  60

Leu Tyr Ser Gly Val Pro Ser Arg Phe Ser Gly Ser Arg Ser Gly Thr
 65                  70                  75                  80

Asp Phe Thr Leu Thr Ile Ser Ser Leu Gln Pro Glu Asp Phe Ala Thr
                85                  90                  95

Tyr Tyr Cys Gln Gln His Tyr Thr Thr Pro Pro Thr Phe Gly Gln Gly
            100                 105                 110

Thr Lys Val Glu Ile Lys Gly Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Ala Ala Ser Gly Phe
145                 150                 155                 160

Asn Ile Lys Asp Thr Tyr Ile His Trp Val Arg Gln Ala Pro Gly Lys
                165                 170                 175

Gly Leu Glu Trp Val Ala Arg Ile Tyr Pro Thr Asn Gly Tyr Thr Arg
            180                 185                 190

Tyr Ala Asp Ser Val Lys Gly Arg Phe Thr Ile Ser Ala Asp Thr Ser
        195                 200                 205

Lys Asn Thr Ala Tyr Leu Gln Met Asn Ser Leu Arg Ala Glu Asp Thr
    210                 215                 220

Ala Val Tyr Tyr Cys Ser Arg Trp Gly Gly Asp Gly Phe Tyr Ala Met
225                 230                 235                 240

Asp Tyr Trp Gly Gln Gly Thr Leu Val Thr Val Ser Ser Ala Ala Ala
                245                 250                 255

Leu Glu His His His His His His Gly Gly Cys
            260                 265

<210> SEQ ID NO 5
<211> LENGTH: 257
<212> TYPE: PRT
<213> ORGANISM: Artificial Sequence
<220> FEATURE:
<223> OTHER INFORMATION: scFv-WT

<400> SEQUENCE: 5

Met Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
 65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125
```

```
Glu Ser Gly Gly Gly Leu Val Gln Pro Gly Gly Ser Leu Arg Leu Ser
            130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Ala Ala Ala Leu Glu His His His His His His Gly Gly
            245                 250                 255

Cys

<210> SEQ ID NO 6
<211> LENGTH: 262
<212> TYPE: PRT
<213> ORGANISM: Artificial Sequence
<220> FEATURE:
<223> OTHER INFORMATION: scFv-CM

<400> SEQUENCE: 6

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
            130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240
```

Val Ser Ser Ala Ala Ala Gly Pro Leu Gly Val Arg Gly Cys Leu Glu
            245                 250                 255

His His His His His His
            260

<210> SEQ ID NO 7
<211> LENGTH: 275
<212> TYPE: PRT
<213> ORGANISM: Artificial Sequence
<220> FEATURE:
<223> OTHER INFORMATION: scFv-NPM

<400> SEQUENCE: 7

Met Ser Gly Gly Gly Ser Gly Gly Ser Gly Pro Leu Gly Val Arg
1               5                   10                  15

Gly Ala Met Asp Ile Gln Met Thr Gln Ser Pro Ser Ser Leu Ser Ala
                20                  25                  30

Ser Val Gly Asp Arg Val Thr Ile Thr Cys Arg Ala Ser Gln Asp Val
            35                  40                  45

Asn Thr Ala Val Ala Trp Tyr Gln Gln Lys Pro Gly Lys Ala Pro Lys
50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Pro Gly Ser Leu Arg
145                 150                 155                 160

Leu Ser Cys Ala Ala Ser Gly Phe Asn Ile Lys Asp Thr Tyr Ile His
                165                 170                 175

Trp Val Arg Gln Ala Pro Gly Lys Gly Leu Glu Trp Val Ala Arg Ile
            180                 185                 190

Tyr Pro Thr Asn Gly Tyr Thr Arg Tyr Ala Asp Ser Val Lys Gly Arg
        195                 200                 205

Phe Thr Ile Ser Ala Asp Thr Ser Lys Asn Thr Ala Tyr Leu Gln Met
    210                 215                 220

Asn Ser Leu Arg Ala Glu Asp Thr Ala Val Tyr Tyr Cys Ser Arg Trp
225                 230                 235                 240

Gly Gly Asp Gly Phe Tyr Ala Met Asp Tyr Trp Gly Gln Gly Thr Leu
                245                 250                 255

Val Thr Val Ser Ser Ala Ala Ala Leu Glu His His His His His
            260                 265                 270

Gly Gly Cys
        275

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

```
Gly Gly Gly Ser Gly Gly Gly Ser
1               5
```

COMPOUND

BACKGROUND OF THE INVENTION

1. Field of the Invention

The present invention relates to compounds and a process for producing the compounds.

2. Description of the Related Art

In order to detect lesion markers present at lesion sites, imaging contrast agents for in vivo diagnosis have been developed. Some of the imaging contrast agents are compounds having lesion marker binding molecules such as antibodies labeled with physical signal generating molecules. As the signal generating molecules, such as radioactive nuclides, molecules which emit magnetic resonance imaging (MRI) signals, molecules which emit supersonic wave signals and molecules which emit fluorescence signals have been known. To detect lesion sites and lesion markers, such an imaging contrast agent is administered to a living body and the signal from the signal generating molecule within the agent is detected from outside the body.

However, when such a compound as above is administered to the blood, the compound may bind to lesion markers present at sites other than the lesion sites, for example, lesion markers escaping from the lesion sites and present in the blood and lesion markers present at normal sites and consequently the amount of the compound which reaches the lesion sites may decrease. Also, in such a case, high contrast detection of the lesion sites is difficult because the compound bound to sites other than the lesion sites and detected as background signal.

To solve the problem mentioned above, Lauffer et al. reported prodrug imaging contrast agents which were made biologically active in vivo in the presence of specific biological activity (Japanese Patent Application Laid-Open No. 2000-507577). The prodrug imaging contrast agents disclosed in this document are those in which a target molecule having a signal generating molecule is bound with a molecule which reduces the binding ability of the target molecule through an enzyme-cleavable linker. The linker is cleaved in a reaction with an alkali phosphatase and, as a result, the binding ability of a low molecular weight compound used as a target molecule with human serum albumin increases as compared with that prior to the cleavage. Lauffer et al. also reported that the cleavage of the linker changed the signal of the MRI signal generating molecule and the detection of the lesion sites were enabled with higher contrast.

Antibodies are molecules which specifically recognize antigens. Antibodies are preferably used for the detection of lesion sites or treatment. Japanese Patent Application Laid-Open No. 2000-507577 describes the possibility of using a low molecular weight compound as a imaging contrast agent but does not disclose the molecular design and the preparation method of the imaging contrast agent, and thus the utility of the imaging contrast agent using an antibody which is made biologically active in vivo has not been known.

SUMMARY OF THE INVENTION

When the detecting an antigen (lesion marker) present at the lesion sites is performed using a compound containing an antibody, the antibody binds to the antigen present at sites other than lesion sites and consequently the amount of the antibody compound which reaches the lesion sites decreases, and signals (background) from the antibody compound bound to the antigen at sites other than the lesion sites occur. As a result, the detection of the lesion sites with high sensitivity and high contrast is difficult, and a compound solving this problem is demanded.

The compound according to a first aspect of the present invention including a polymer represented by general formula (1):

$$L\text{-}Y\text{-}A \tag{1}$$

wherein, A is a single-chain antibody moiety, which is a polypeptide including an antigen-binding site; L is a linker moiety, which is a polypeptide including a protease cleavage site; Y is a peptide moiety, which including 0 or more amino acids connecting the linker moiety L with the single-chain antibody moiety A; and the linker moiety L binds to an N terminus of the peptide moiety Y or an N terminus of the single-chain antibody moiety A.

The compound according to a second aspect of the present invention including a polymer represented by general formula (2):

$$X\text{-}L\text{-}Y\text{-}A \tag{2}$$

wherein, A is a single-chain antibody moiety, which is a polypeptide including an antigen-binding site; L is a linker moiety, which is a polypeptide including a protease cleavage site; Y is a peptide moiety, which including 0 or more amino acids connecting the linker moiety L with the single-chain antibody moiety A; the linker moiety L binds to an N terminus of the peptide moiety Y or an N terminus of the single-chain antibody moiety A; and X is either one of polyethylene glycol, an organic dye, an organic polymer and a particle.

The process for producing a compound according to a third aspect of the present invention is a process for producing a compound including a polymer represented by general formula (1), including inserting to a plasmid a nucleic acid which has a base sequence encoding a single-chain antibody moiety A, a base sequence encoding a linker moiety L and a base sequence encoding a peptide moiety Y; introducing to bacteria the plasmid in which the nucleic acids are inserted; and collecting a compound expressed by the bacteria to which the plasmid is introduced:

$$L\text{-}Y\text{-}A \tag{1}$$

wherein, A is single-chain antibody moiety, which is a polypeptide including an antigen-binding site; L is a linker moiety, which is a polypeptide comprising a protease cleavage site; Y is a peptide moiety, which including 0 or more amino acids connecting the linker moiety L with the single-chain antibody moiety A; and the linker moiety L binds to an N terminus of the peptide moiety Y or an N terminus of the single-chain antibody moiety A.

The compound of the present invention is in a condition in which the binding ability with the antigen in the single-chain antibody moiety is reduced at sites other than the lesion sites while the binding ability is recovered at the lesion sites. The decrease in the amount of the single-chain antibody moiety which reaches the lesion sites due to the binding with the antigens present at the sites other than the lesion sites can be suppressed by using the compound of the present invention. Also signals (background) from single-chain antibody moieties bound to the antigens present at the sites other than the lesion sites can be suppressed by using the compound of the present invention. Therefore, high contrast detection of the lesion sites is thereby enabled by the present invention.

Further features of the present invention will become apparent from the following description of exemplary embodiments with reference to the attached drawings.

DESCRIPTION OF THE EMBODIMENTS

Figure 1:
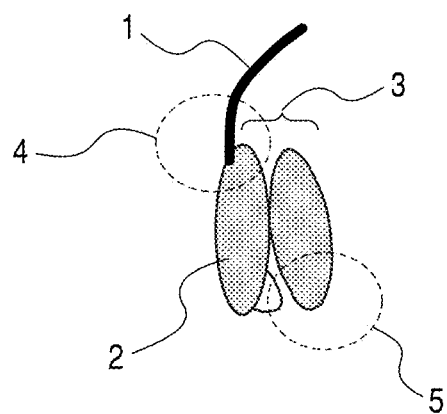
FIG. 1 is a schematic view of the compound provided by the present invention.

Preferred embodiments of the present invention will now be described in detail in accordance with the accompanying drawings.

The First Embodiment

The compound according to the first embodiment according to the present invention including a polymer represented by general formula (1):

$$L-Y-A \quad (1)$$

wherein, A is a single-chain antibody moiety, which is a polypeptide including an antigen-binding site; L is a linker moiety, which is a polypeptide including a protease cleavage site; Y is a peptide moiety, which including 0 or more amino acids connecting the linker moiety L with the single-chain antibody moiety A; and the linker moiety L binds to an N terminus end of the peptide moiety Y or an N terminus of the single-chain antibody moiety A.

The compound according to this embodiment has a single-chain antibody moiety, a linker moiety and a peptide moiety. The linker moiety is bound to the N terminus of the peptide moiety, and the peptide moiety is bound to the N terminus of the single-chain antibody moiety. Alternatively, the linker moiety is bound to the N terminus of the single-chain antibody moiety directly (in the case where the peptide moiety has 0 amino acid). In this constitution, antigen binding ability of the single-chain antibody moiety is inhibited or reduced, and when the linker moiety is cleaved by protease, the antigen binding ability of the single-chain antibody moiety is recovered.

In this embodiment, the statement that the "antigen binding ability is inhibited or reduced" means that the ability of binding with an antigen of the single-chain antibody moiety in an unmodified state is lost or weakened by some kind of factors. In the meantime, the statement that the "antigen binding ability is recovered" means that the lost or weakened antigen binding ability improves to the same or similar level as that of the single-chain antibody moiety in an unmodified state.

(Single-Chain Antibody Moiety)

In the present invention, the single-chain antibody moiety is a polypeptide comprising a site (antigen-binding site) in which a light chain variable (VL) domain and a heavy chain variable (VH) domain of the antibody are linked with a linker comprising peptides.

Here, the antibody may be derived from human, mouse, rat, camel, bird and the other unlimited origins, and besides, it may be a chimeric antibody, a polyclonal antibody or a monoclonal antibody.

The antibody mentioned above can be used without limitation, but in view of the objects of the present invention, examples thereof include antibodies bound to lesion markers selected from a group including EGFR family, VEGF family, VEGFR family, PSA, CEA, matrix metalloprotease family, EGF family, integrin family, selectin family, endoglin or MUC family and antibodies binding to HER2.

The single-chain antibody moieties can be simply and readily prepared at inexpensive cost as compared with various other antibodies and since they have a smaller molecular weight as compared with normal antibodies (whole antibodies, etc.), they are likely to be immediately excreted to the outside of the body and besides they readily reach the lesion sites. Therefore, the single-chain antibody moieties are used for the detection or treatment of the lesion sites.

The single-chain antibody moiety is, for example, a polypeptide containing the following amino acid sequence.

```
                                              (SEQ ID NO: 1)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGGGGSGGGGSGGGGSEVQLVESGGGLVQPGGSLRLSCAASGFN

IKDTYIHWVRQAPGKGLEWVARIYPTNGYTRYADSVKGRFTISADTSKNT

AYLQMNSLRAEDTAVYYCSRWGGDGFYAMDYWGQGTLVTVSS
```

Any amino acid may be linked to the C terminus of the single-chain antibody moiety.

(Linker Moiety)

In the present invention, the linker moiety refers to a polypeptide comprising a protease cleavage site. Here, the "protease cleavage site" means a site having an amino acid sequence specifically recognized by protease, and thereby the amino acid sequence is recognized by protease in an activated state, and specifically hydrolyzed to be cleaved.

The protease is preferably one from matrix metalloprotease family or serine protease family, and, examples thereof include matrix metalloprotease-2 (MMP-2), matrix metalloprotease-9 (MMP-9), prostate specific antigen (PSA), plasmin, cathepsin, caspase as the target protease.

As for the protease cleavage site, polypeptides containing amino acid sequence PLGVR (SEQ ID NO: 2) can be used as a cleavage site of MMP-2. In addition, polypeptides containing amino acid sequence SSIYSQTEEQ (SEQ ID NO: 3) can be used as a cleavage site of PSA.

Any amino acid may be bound to the N terminus of the linker moiety.

(Peptide Moiety)

In the present invention, the peptide moiety comprises 0 or more amino acids connecting the linker moiety with the single-chain antibody moiety. The number of the amino acids is preferably not more than 20, and more preferably not more than 10. When the number of the amino acids exceeds 20, when the protease cleavage site is cleaved by protease, there is a risk that the antigen binding ability of the single-chain antibody moiety may remain inhibited or reduced.

This embodiment is described in more detail by way of FIG. 1. FIG. 1 is a schematic view of the compound according to this embodiment. The peptide moiety is, however, not illustrated it in FIG. 1. There are shown a linker moiety 1, a single-chain antibody moiety 2, an antigen-binding site 3, an N terminus 4 and a C terminus 5 in FIG. 1.

Various kinds of mechanisms can be presumed as the mechanism to inhibit or decrease the antigen binding ability. Firstly, it is presumed that the linker moiety bound to the N terminus of the peptide moiety or the single-chain antibody moiety is present between the antigen-binding site of the single-chain antibody moiety and antigens causing steric hindrance. In this case, it is presumed that the linker moiety covers up the antigen-binding site of the single-chain antibody moiety, and the other antibodies cannot be linked to the antigens.

The reason for binding the linker moiety to the N terminus of the single-chain antibody moiety is as follows. Firstly, when the linker moiety is bound to the linker which links a heavy chain variable (VH) domain and light chain variable (VL) domain in the single-chain antibody moiety, the structure of the single-chain antibody moiety in itself changes, and the structure does not restore the original structure after the linker moiety is cleaved and as a result, there is a risk that the antigen binding ability might not recover. On the other hand, it is presumed that when the linker moiety is bound to either end of the single-chain antibody moiety, the structure is hardly affected, and after the linker moiety is cleaved, the single-chain antibody moiety readily recovers the structure before the single-chain antibody moiety introduces the linker moiety, and thus the antigen binding ability is easy to recover after the linker moiety is cleaved. Therefore, it is effective to introduce the linker moiety into either end of the single-chain antibody moiety because the antigen binding ability after the cleavage of the linker moiety recovers to the same or similar level as that before the linker moiety is introduced. Next, the N terminus of the single-chain antibody moiety is closer to the antigen-binding site than the C terminus. Therefore it is presumed that when the linker moiety is bound to the N terminus of the single-chain antibody moiety, the effects such as steric hindrance action at or around the antigen-binding site of the single-chain antibody moiety is caused more efficiently even though the length of the linker moiety is short than the case where the linker moiety is bound to the C terminus of the single-chain antibody moiety, and that is, the antigen binding ability can be reduced more strongly. It is thereby presumed that inhibition or reduction of the antigen binding ability can be decreased without excessively increasing the molecular weight of the compound. Suppressing the excessive increase in the molecular weight of the compound is effective since such suppression enables the compound to maintain the nature similar to the compound only including the single-chain antibody moiety that the compound is readily excreted to the outside of the body immediately while it is easy to reach the lesion sites. Furthermore, introducing the linker moiety to the N terminus of the single-chain antibody moiety is effective since the N terminus of the single-chain antibody moiety is close to the antigen-binding site and thus such introduction enables the reduction of the antigen binding ability more strongly than the introducing to the C terminus. In addition, when the linker moiety is introduced to the N terminus of the single-chain antibody moiety, it is possible to link other molecules to the C terminus remote from the antigen-binding site and, for example, it is possible to link signal generating molecules and therapeutic agent without impairing the antigen binding ability. It is presumed from the above that it is the most effective to bind the linker moiety to the N terminus of the single-chain antibody moiety.

The same holds true when the linker moiety is bound to the N terminus of the peptide moiety and the peptide moiety is bound to the N terminus of the single-chain antibody moiety.

(Signal Generating Molecule)

In the compound according to this embodiment, a signal generating molecule can be bound to the single-chain antibody moiety.

Various kinds of molecules can be used for the signal generating molecule such as radionuclides, molecules which emit MRI signals, molecules which emit supersonic wave signals and molecules which emit fluorescence signals. For example, for the signal generating molecules which absorb light and give off supersonic wave signals or light signals, Alexa Fluor 680, Alaxa Fluor 700, Alexa Fluor 750, Alexa Fluor 790 (trademarks, Invitrogen Corp.), Cy 5, Cy 5.5, Cy 7 (trademarks, GE Health Care), HiLyte 647, HiLyte 680, HiLyte 750 (trademarks, AnaSpec, Inc), DY-680, DY-700, DY-730, DY-750, DY-782 (trademarks, Dyomics, Jena, Germany) can be used. It is also effective to select near infrared light absorption pigments which absorb the light of near infrared wavelength range of about 600 nm or more and about 1,000 nm or less excellent in living body permeability for the molecules which absorb light and give off supersonic wave signals or light signals. In addition, various kinds of particles can be used for particles such as particles of metals and metal oxides such as iron oxide particles, gold particles, gold nanorods, platinum and silver. Furthermore, it is possible to bind therapeutic agents such as anticancer agents to the single-chain antibody moiety of this embodiment so as to deliver the therapeutic agents to the lesion sites and reduction of the side effect can be expected by reducing the deliver of the therapeutic agents to the sites other than the lesion sites.

Among compounds of the present invention, those to which signal generating molecules are linked can be also used for the detection of the lesion markers. That is, a process for detecting lesion markers is provided which comprises administering to an individual a compound of the present invention to which a signal generating molecule is linked or adding such a compound to a sample obtained from an individual and detecting signals, thereby detecting presence or absence of lesion markers or presence or absence of lesion sites generating lesion markers in the individual or in the sample obtained from an individual. The detection methods of the lesion markers are as follows. That is, a compound of the present invention to which a signal generating molecule is bound is administered to an individual or added to a sample obtained from an individual such as the internal organs. Here, the term individual is not particularly limited to human or mammals such as experimental animals or pets but refers to all the creatures and inside individual or the sample obtained from an individual includes internal organs, tissues and tissue slices. After the administration or addition, signals of signal generating molecules contained in the individual or the sample are detected with a measuring instrument which can detect signal generating molecules. As a result, when signals are detected in a level higher the threshold values as a standard, it can be estimated that a lesion marker or a lesion site generating a lesion marker is present in the individual or that a lesion marker is present in the sample or a lesion site generating a lesion marker is present in the individual from which the sample is derived.

(Imaging)

Similarly, among compounds of the present invention, those to which a signal generating molecule is linked can be used for imaging the lesion marker. The imaging methods of the lesion marker are as follows. That is, a compound of the present invention is administered to an individual or added to a sample obtained from an individual and detecting signals, and thereby imaging as to presence/absence of a lesion marker in the individual or the sample obtained from an individual or presence/absence of a lesion site generating a lesion marker can be performed.

The Second Embodiment

In the following, the compound according to the second embodiment of the present invention is described but description about what is common with the first embodiment is omitted.

The compound according to the second embodiment of the present invention including a polymer represented by general formula (2):

wherein, A is a single-chain antibody moiety, which is a polypeptide including an antigen-binding site; L is a linker moiety, which is a polypeptide comprising a protease cleavage site; Y is a peptide moiety, which including 0 or more amino acids connecting the linker moiety L with the single-chain antibody moiety A; the linker moiety L binds to an N terminus of the peptide moiety Y or an N terminus of the single-chain antibody moiety A; and X is either one of polyethylene glycol, an organic dye, an organic polymer and a particle.

The compound according to this embodiment has a single-chain antibody moiety, a linker moiety, a peptide moiety and a site (X in Formula (2)) which can cover the antigen-binding site of the single-chain antibody moiety. The linker moiety is bound to N terminus of the peptide moiety, and the peptide moiety is bound to the N terminus of the single-chain antibody moiety. Alternatively, the linker moiety is bound to the N terminus of the single-chain antibody moiety directly (in the case where the peptide moiety has 0 amino acid). In this constitution, antigen binding ability of the single-chain antibody moiety is inhibited or reduced, and when the linker moiety is cleaved, the antigen binding ability of the single-chain antibody moiety is recovered.

The site which can cover up the antigen-binding site is either one of polyethylene glycol (hereinbelow abbreviated as PEG), an organic dye, an organic polymer and a particle. For the organic dye, Alexa Fluor 680, Alaxa Fluor 700, Alexa Fluor 750, Alexa Fluor 790 (trademarks, Invitrogen Corp.), Cy 5, Cy 5.5, Cy 7 (trademarks, GE Health Care), HiLyte 647, HiLyte 680, HiLyte 750 (trademarks, AnaSpec, Inc), DY-680, DY-700, DY-730, DY-750, DY-782 (trademarks, Dyomics, Jena, Germany), etc. can be used. For the organic polymer, polylactic acid (Polylactic acid, PLA), polylactic acid glycolic acid copolymer (Poly(DL-lactic-co-glycolic acid), PLGA), etc. can be used.

Figure 2:
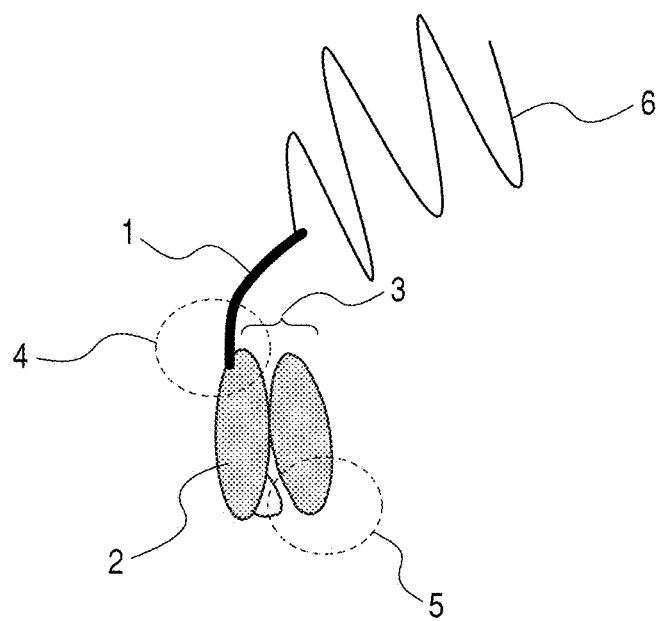
FIG. 2 is a schematic view of a compound in which polyethylene glycol (PEG) is bound to the N terminus of a single-chain antibody moiety through a linker moiety.

FIG. 2 illustrates the case where PEG is introduced as a schematic view. The peptide moiety is, however, not illustrated in FIG. 2. There are shown a linker moiety 1, a single-chain antibody moiety 2, an antigen-binding site 3, an N terminus 4, a C terminus 5 and PEG 6 in FIG. 2. It is supposed that it is effective that the site which can cover the linker moiety and the linked antigen-binding site is bound to the N terminus of the single-chain antibody moiety even when these molecules are use. For example, PEG is particularly preferably used as the site which can cover up the antigen-binding site, and it is supposed that PEG is present in a sterically expanded state in an aqueous solution. Therefore, it is presumed that when the linker moiety and the linked PEG were introduced to the N terminus of the single-chain antibody moiety, PEG is present between the antigen-binding site of the single-chain antibody moiety and the antigens, it causes larger steric hindrance, as compared with, for example, the case where it is introduced to the other site than the N-terminal site such as C-terminal site and thereby the action to inhibit or reduce the antigen binding ability becomes larger, and it is enabled to reduce the antigen binding ability of the single-chain antibody moiety more strongly.

Various kinds of effects can be expected from the introduction of PEG in addition to the inhibition of the antigen-binding ability, etc. Examples of such effects include regulation of the molecular weight of the compound and regulation of the protein adsorption ability of the compound by introducing PEG. Since the linker moiety is not cleaved and PEG is not detached from the compound having PEG introduced thereto in blood before the compound reaches the lesion site, the molecular weight of the compound is maintained as large and the protein adsorbing ability of the compound is suppressed. Thereby, the compound is maintained at a size larger than that to be excreted from the kidney and the loss of the compound by the excretion from the kidney is suppressed. The loss of the compound by excretion via such as liver which removes the compound to the outside of the body through adsorption of protein is also suppressed. On the other hand, the linker moiety is cleaved at the lesion sites, and the molecular weight of the compound decreases because PEG is detached. This would also enhance the penetrative properties of the compound at the lesion sites as compared with the sites other than the lesion sites so that the compound may penetrate to the depth of the sites and thereby enable improvement in the accumulation of the compound at the lesion sites. In contrast, the compound does not penetrate to the depth of the normal sites since the linker moiety is not cleaved and PEG is not detached at the normal sites. On this account, it would be possible that signals (background) which occur by the accumulation of the compound at the normal sites is reduced.

It is preferable that the molecular weight of PEG is not less than 20 kDa. It is also preferable that the molecular weight of PEG is not more than 40 kDa.

In the case where the enzyme which cleaves the linker moiety is identical with the lesion marker to which the single-chain antibody moiety binds, it would be possible that both the presence and the activity of the enzyme are detected at the same time. In addition, when the enzyme which cleaves the linker moiety is specific to the lesion sites and the enzyme is different from the lesion marker to which the single-chain antibody moiety binds, the compound only accumulates at the lesion sites only in the case where the two kinds of the lesion markers at the lesion sites are present, it would be possible that the position precision is improved and a detailed position information of the lesion sites is detected. For example, in the case of combination of a single-chain antibody moiety which binds to HER2 and a linker moiety which contains a cleavage site of MMP-2, it would be possible that tumors which show both the two conditions that HER2, poor prognosis factor of cancers, is positive and that MMP-activity as an index showing properties such as metastasis and invasion is high, that is, tumors appearing to be highly malignant, are detected with high position accuracy. In this case, soluble HER2 present in blood or the other fluid and HER2 positive/MMP-2 negative tumor sites are hard to be detected with the imaging contrast agent, it would be enabled that background is reduced. In addition, in the case of combination of a single-chain antibody moiety which binds to vascular endothelium growth factor VEGF and a linker moiety which contains a cleavage site of MMP-2, since the present compound is hard to bind to the VEGF seeping into blood while it is easy to bind to the VEGF present in high concentration at lesion sites where activated MMP-2 is present, lesion sites where angiogenesis is active and VEGF is present in high concentration are detected with high position accuracy.

The Third Embodiment

The third embodiment of the present invention is described. This embodiment relates to a process for producing the compound comprising a polymer represented by the general formula (1) mentioned above. Specifically, the process has the following steps.
(i) A step of inserting to a plasmid a nucleic acid which has a base sequence encoding a single-chain antibody moiety A, a base sequence encoding a linker moiety L and a base sequence encoding a peptide moiety Y;
(ii) A step of introducing to bacteria the plasmid in which the nucleic acid is inserted; and
(iii) A step of collecting a compound expressed by the bacteria to which the plasmid is introduced.

Here, the process for producing the compound according to this embodiment may include a step other than the steps (i) to (iii) mentioned above.

EXAMPLES

In the following, the present invention is described by way of examples so as to clarify the characteristic of the present invention in more detail. It should be noted, however, that the other combinations of the moieties of the single-chain antibody moiety, the linker moiety and the site which can cover the antigen-binding site can be used in the present invention and that the present invention is not limited to these examples.

Example 1

Preparation of Hu4D5-8 Scfv

Firstly, based on the gene sequence of the variable region of IgG which binds to HER2, the gene fragment which encoded a single-chain antibody (scFv) moiety was prepared. An amino acid sequence PLGVR which was specifically cleaved by MMP-2 was bound to the N terminus of the prepared gene, and a 6×His tag comprising 6 consecutive histidines for protein purification was bound to the C terminus and further 2 glycines as a spacer and a cysteine for introducing a signal generating molecule were disposed in the downstream thereof. As a comparison, a gene which did not contain in the C terminus the amino acid sequence PLGVR which is specifically cleaved by MMP-2 was prepared in the same way. A plasmid pET-22b (+) (Novagen Corporation) in which the above gene fragment was inserted in the downstream of the T7 promoter was introduced into *E. coli* (*Escherichia coli* BL21 (DE3) to obtain a strain for expression. After the obtained strain was cultivated in 4 ml of LB-Amp culture medium overnight, the whole volume was added to 250 ml of 2×YT culture medium and subjected to shaken cultivation at 120 rpm, 28° C. for 8 hours. Then, IPTG was added in the final concentration of 1 mM and the mixture was cultivated at 28° C. overnight. The cultivated *E. coli* was centrifuged at 8000× g, 4° C. for 30 minutes and the supernatant of the culture solution was collected. Ammonium sulfate was added to the obtained culture solution in an amount of 60% by weight and the proteins were precipitated by salting out. After the salted out solution was left standstill at 4° C. overnight, sediments were collected by centrifuging the solution at 8000×g, 4° C. for 30 min. The obtained sediments were dissolved in 20 mM Tris.HCl/500 mM NaCl buffer, and 1 L of the buffer was dialyzed. The protein solution after the dialysis was added to a column filled with His.Bind® and Resin (Novagen Corporation) and purified by metal chelate affinity chromatography with Ni ion. It was confirmed that the purified hu4D5-8 scFv with an MMP-2 substrate introduced at the N terminus (scFv-NM) and hu4D5-8 scFv without an MMP-2 substrate at the N terminus (scFv-WT) showed a single band and had a molecular weight of about 28 kDa in SDS-PAGE.

The prepared scFv-NM had the following sequence.

```
                                             (SEQ ID NO. 4)
MSGPLGVRGAMDIQMTQSPSSLSASVGDRVTITCRASQDVNTAVAWYQQK

PGKAPKLLIYSASFLYSGVPSRFSGSRSGTDFTLTISSLQPEDFATYYCQ

QHYTTPPTFGQGTKVEIKGGGGSGGGGSGGGGSEVQLVESGGGLVQPGGS

LRLSCAASGFNIKDTYIHWVRQAPGKGLEWVARIYPTNGYTRYADSVKGR

FTISADTSKNTAYLQMNSLRAEDTAVYYCSRWGGDGFYAMDYWGQGTLVT

VSSAAALEHHHHHHGGC
```

The prepared scFv-WT had the following sequence.

```
                                             (SEQ ID NO. 5)
MDIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTFG

QGTKVEIKGGGGSGGGGSGGGGSEVQLVESGGGLVQPGGSLRLSCAASGF

NIKDTYIHWVRQAPGKGLEWVARIYPTNGYTRYADSVKGRFTISADTSKN

TAYLQMNSLRAEDTAVYYCSRWGGDGFYAMDYWGQGTLVTVSSAAALEHH

HHHHGGC
```

Example 2

Confirmation of Cleavage of scFv-NM at the Linker Moiety by the Addition of MMP-2

Figure 3:
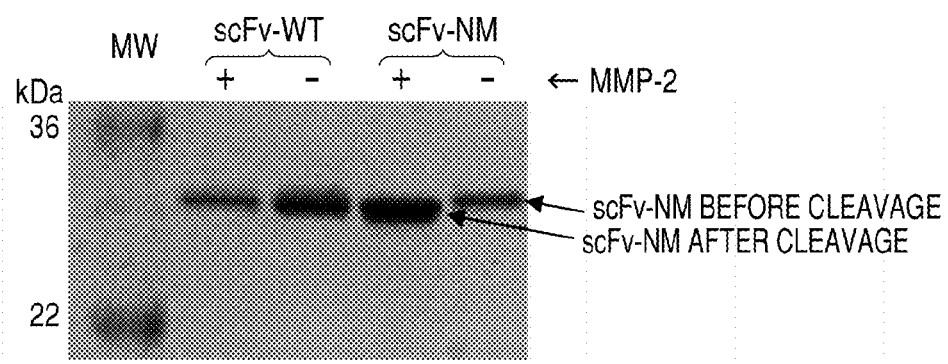
FIG. 3 illustrates the results of reduced type SDS-PAGE of prepared scFv-NM and scFv-WT samples with and without addition of MMP-2.

Change in the molecular weight resulted from the cleavage of the peptide by the addition of MMP-2 to the scFv-NM prepared above was measured. 0.10 mg/ml of an active type MMP-2 (Cosmo Bio Co., Ltd.) was added in about 15 nM to about 4 µM of PEGylated scFv dialyzed in a TCNB buffer (50 mM Tris, 10 mM $CaCl_2$, 150 mM NaCl, 0.05% Brij 35, pH 7.5), and the reaction was performed for about 20 hours and the change in the molecular weight was measured by reduced type SDS-PAGE. As a result, decrease in the molecular weight was detected in scFv-NM by adding MMP-2 as shown in FIG. 3. On the other hand, decrease in the molecular weight was not detected in scFv-WT. It was confirmed from the above that the peptide of scFv-NM was cleaved by MMP-2.

Example 3

Confirmation of Improvement in the Antigen Binding Ability of scFv-NM by the Addition of MMP-2)

Figure 4:
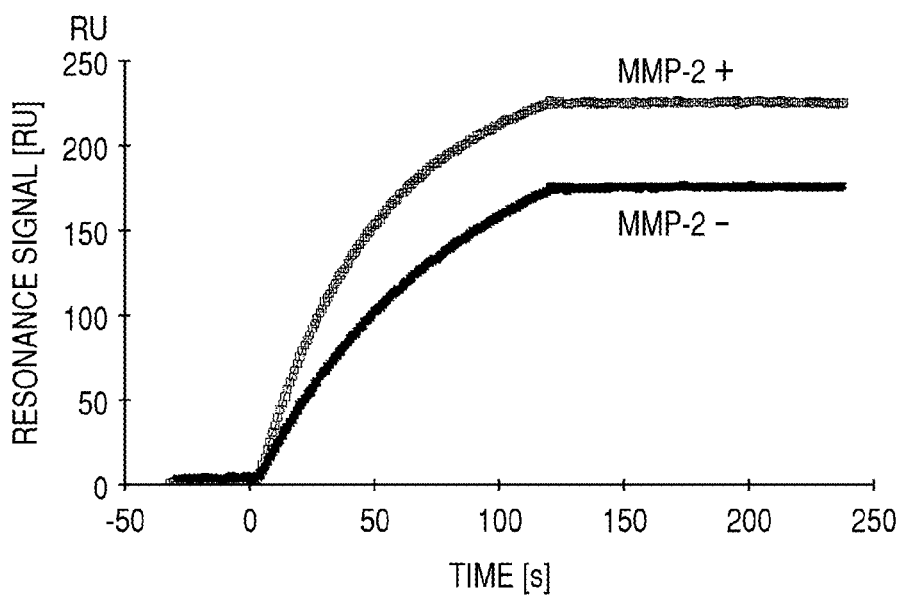
FIG. 4 illustrates the results of the measurement of interaction of the prepared scFv-NM with HER2 before and after the addition of MMP-2 using a Biacore X system.

The interaction of scFv-NM, scFv-WT prepared above with HER2, which was an antigen, was measured using Biacore X system (GE Healthcare Co., Ltd.) and the change in the binding ability of scFv before and after the addition of MMP-2 was measured. As an antigen, Recombinant Human ErbB2/Fc Chimera (with R & D Systems, Inc.) was immobilized to the carboxymethyldextran chain on the surface of CM-5 chip by amine coupling according to the recommendation of the manufacture. The immobilized amount was about 1,000 R U. As a running buffer, PBS-T (2.68 mM KCl/137 mM NaCl/1.47 mM KH$_2$PO$_4$/1 mM Na$_2$HPO$_4$/0.005% Tween 20, pH 7.4) was used and 50 nM scFv was injected under a condition of 20 µL/min in the flow rate, and the binding ability was evaluated. As a result, as shown in FIG. 4, change in the sensor gram was able to be confirmed before and after the addition of MMP-2 and it was found that the antigen binding ability of scFv-NM was improved. On the other hand, it was confirmed that the antigen binding ability of scFv-WT hardly changed in MMP-2 before and after the addition of MMP-2.

Example 4

Preparation of scFv-NM with PEGylated N Terminus

After the buffer of the scFv-NM prepared in Example 1 was substituted with 100 mM phosphate buffer (pH 5.0), PEG-aldehyde (Nichiyu Co., Ltd.) of 5 kDa, 20 kDa or 40 kDa in 40-time molar amount was added to the scFv-NM. 2-Picoline borane was added in the final concentration of 20 mM and the reaction was performed at 4° C. for about 3 days. After the reaction, the buffer was changed to a TCNB buffer (50 mM Tris, 10 mM CaCl$_2$, 150 mM NaCl, 0.05% Brij 35, pH 7.5) and the fraction in which 1 molecular of PEG was supposed to be bound was separated by gel filtration chromatography with Superdex 200 GL 10/300 column (GE Healthcare Co., Ltd.) and scFv-NM in which the N terminus was supposed to be PEGylated was obtained.

Example 5

Figure 5:
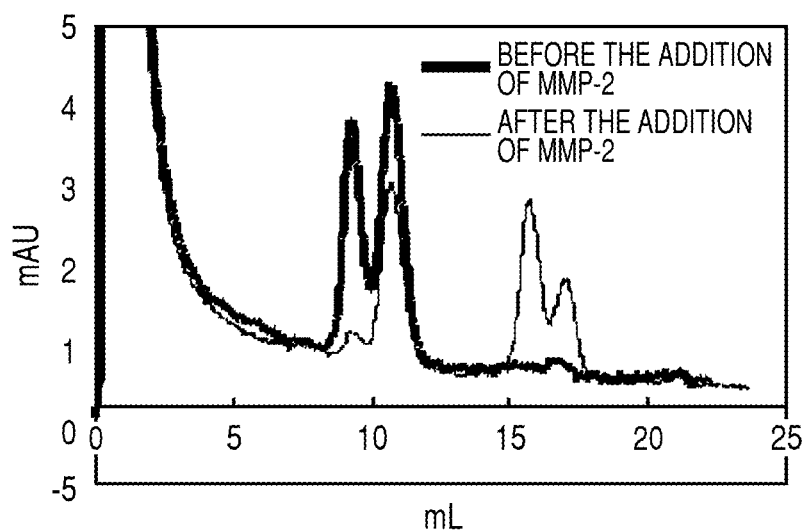
FIG. 5 illustrates the results of the molecular state of the prepared N-terminally PEGylated scFv-NM detected in gel filtration chromatography before and after the addition of MMP-2.

Confirmation of the Detachment of PEG by the Addition of MMP-2 from scFv-NM with PEGylated N Terminus Change in the molecular weight of the scFv-NM prepared above in which the N terminus was supposed to be PEGylated was evaluated by the addition of MMP-2. 0.10 mg/ml of an active type MMP-2 (Cosmo Bio Co., Ltd.) was added in about 10 nM in the final concentration to the scFv-NM in which the N terminus was supposed to be PEGylated, which was dissolved in a TCNB buffer and the reaction was performed for about 20 hours and the change in the molecular weight was evaluated by gel filtration chromatography with Superdex 200 GL 10/300 column. The result of the gel filtration chromatography (absorption at 280 nm monitored) of 20-kDa PEGylated scFv-NM before and after the addition of MMP-2 was shown in FIG. 5. Two peaks which were not present before the cleavage were detected by the addition of MMP-2 as shown in FIG. 5. These are considered as a monomer and a dimer of scFv-NM not modified with PEG. That is, this result shows that PEG, which had modified the N terminus, was detached from scFv-NM by the cleavage by MMP-2 of MMP-2 substrates which was introduced into the N terminus. That is, it was able to be confirmed that the N terminus was modified with PEG. In addition, as a result of comparing the ratio of the peak area which was supposed to correspond to the scFv-NM from which PEG was detached and the total peak area, the ratio that the N terminus was PEGylated among the whole PEGylated scFv-NM PEG was around 50%. As for the remaining 50%, the amino group of the lysine residue in scFv-NM molecules was supposed to be PEGylated. It was also confirmed that about 50% of the N terminus were similarly PEGylated when PEG aldehyde of 5 kDa or 40 kDa was used. It was confirmed from above that scFv-NM with PEGylated N terminus was acquired.

Example 6

Preparation of scFv in which a MMP-2 Substrate was Introduced into the C Terminus Based on gene sequencing of the variable region of IgG which binds to HER2, the gene fragment which encoded a single-chain antibody (scFv) moiety was prepared. An amino acid sequence PLGVR which was specifically cleaved by MMP-2, a cysteine residue for linking a molecule which reduced the antigen-binding ability and a 6×His tag comprising 6 consecutive histidines for protein purification were disposed in the C terminus of the prepared gene. A plasmid pET-22b (+) (Novagen Corporation) in which the above gene fragment was inserted in the downstream of the T7 promoter was introduced into *E. coli* (*Escherichia coli* BL21 (DE3)) to obtain a strain for expression. After the obtained strain was cultivated in 4 ml of LB-Amp culture medium overnight, the whole volume was added to 250 ml of 2×YT culture medium and subjected to shaken cultivation at 120 rpm, 28° C. for 8 hours. Then, IPTG was added in the final concentration of 1 mM and the mixture was cultivated at 28° C. overnight. The cultivated *E. coli* was centrifuged at 8000×g, 4° C. for 30 minutes and the supernatant of the culture solution was collected. Ammonium sulfate was added to the obtained culture solution in an amount of 60% by weight and the proteins were precipitated by salting out. After the salted out solution was left standstill at 4° C. overnight, sediments were collected by centrifuging the solution at 8000×g, 4° C. for 30 min. The obtained sediments were dissolved in 20 mM Tris.HCl/500 mM NaCl buffer, and 1 L of the buffer was dialyzed. The protein solution after the dialysis was added to a column filled with His.Bind® and Resin (Novagen Corporation) and purified by metal chelate affinity chromatography with Ni ion. It was confirmed that the purified scFv with MMP-2 substrate introduced at the C terminus (scFv-CM) showed a single band and had a molecular weight of about 28 kDa in SDS-PAGE.

The prepared scFv-CM had the following sequence.

```
                                            (SEQ ID NO. 6)
MDIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTFG

QGTKVEIKGGGGSGGGGSGGGGSEVQLVESGGGLVQPGGSLRLSCAASGF

NIKDTYIHWVRQAPGKGLEWVARIYPTNGYTRYADSVKGRFTISADTSKN

TAYLQMNSLRAEDTAVYYCSRWGGDGFYAMDYWGQGTLVTVSSAAAGPLG
```

-continued

VRGCLEHHHHHH

Example 7

Preparation of scFv-CM with PEGylated C Terminus

Figure 6:
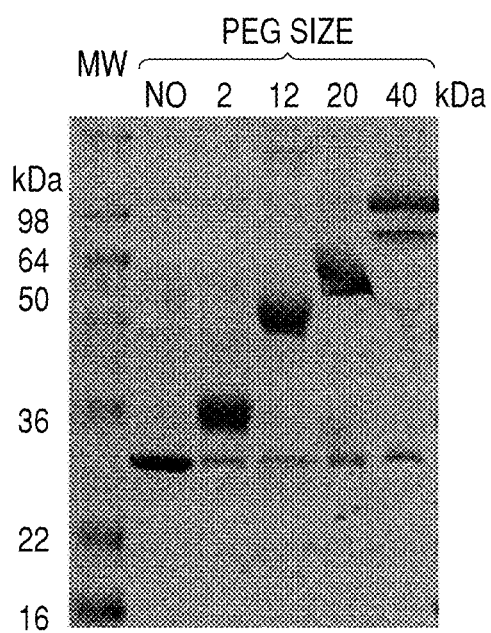
FIG. 6 illustrates the results of reduced type SDS-PAGE of scFv-CM which has been reacted with PEG-maleimide of 2 kDa, 5 kDa, 12 kDa, 20 kDa and 40 kDa.

After the buffer of the scFv-CM prepared above was substituted with a phosphate buffer containing 5 mM EDTA (2.68 mM KCl/137 mM NaCl/1.47 mM $KH_2PO_4$/1 mM $Na_2HPO_4$/5 mM EDTA, pH 7.4), the resultant solution was subjected to reduction treatment with 10- to 20-time molar amount of tris(2-carboxyethyl)phosphine hydrochloride (TCEP) at 25° C. for 2 to 4 hours. This scFv-CM subjected to reduction treatment was reacted with PEG maleimide (Nichiyu Co., Ltd.) of 2 kDa, 5 kDa, 12 kDa, 20 kDa or 40 kDa in 10-time molar amount at 25° C. for 2 to 4 hours. It was confirmed by reduced type SDS-PAGE that these were PEGylated (FIG. 6). After the reaction, unreacted PEG-maleimide was removed by gel filtration chromatography with Superdex 200 GL 10/300 column to obtain scFv-CM with PEGylated C terminus.

Example 8

Figure 7:
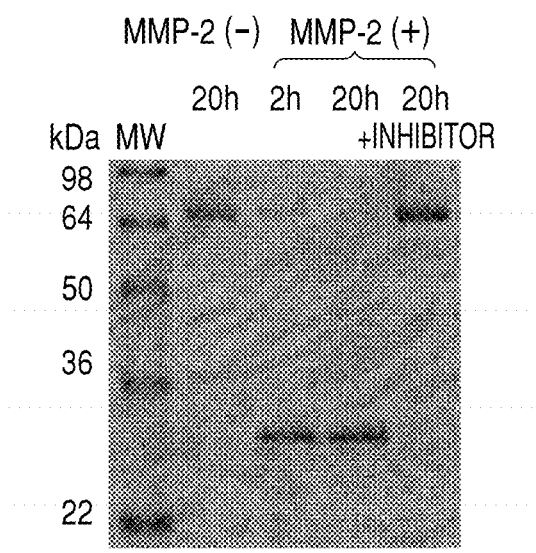
FIG. 7 illustrates the results of reduced type SDS-PAGE of the prepared C-terminally PEGylated scFv-CM with and without addition of MMP-2 and in the presence of MMP-2 activity inhibitor.

Confirmation of the Detachment of PEG by the Addition of MMP-2 from scFv-CM with PEGylated C Terminus For those appended with 20 kDa PEG-maleimide among the scFv-CM with PEGylated C terminus prepared above, change in the molecular weight was evaluated by the addition of MMP-2. An active type MMP-2 (0.10 mg/ml) was added in about 10 nM in the final concentration to the scFv-CM with PEGylated C terminus dialyzed in a TCNB buffer and the reaction was performed for 2 hours and 20 hours and the change in the molecular weight at the respective time point was evaluated by reduced type SDS-PAGE. Another experiment in which 1 mM of 1,10-phenanthroline (Sigma-aldrich), an MMP-2 activity inhibitor was added and the reaction was performed for 20 hours in the same way. As a result, a band was detected in the vicinity of 28 kDa which was the molecular weight of scFv-CM in 2 hours after the addition of MMP-2, and almost scFv-CM was detected as a main band in 20 hours as shown in FIG. 7. The detection of this scFv-CM band was suppressed by the addition of 1,10-phenanthroline. It was confirmed from above that PEG of scFv-CM with PEGylated C terminus was specifically cleaved and detached from scFv-CM by MMP-2.

Example 9

Preparation of scFv in which a Peptide and an MMP Substrate was Introduced to the N Terminus Firstly, based on the gene sequence of the variable region of IgG which binds to HER2, the gene fragment which encoded a single-chain antibody (scFv) moiety was prepared. A peptide GGGSGGGS (SEQ ID NO: 8), and in the downstream thereof an amino acid sequence PLGVR which was specifically cleaved by MMP-2 were disposed in the N terminus of the prepared gene, and in the downstream thereof a 6×His tag comprising 6 consecutive histidines for protein purification and further 2 glycines as a spacer and a cysteine for introducing a signal generating molecule were disposed in the C terminus. A plasmid pET-22b (+) (Novagen Corporation) in which the above gene fragment was inserted in the downstream of the T7 promoter was introduced into *E. coli* (*Escherichia coli* BL21 (DE3)) to obtain a strain for expression. After the obtained strain was cultivated in 4 ml of LB-Amp culture medium overnight, the whole volume was added to 250 ml of 2×YT culture medium and subjected to shaken cultivation at 120 rpm, 28° C. for 8 hours. Then, IPTG was added in the final concentration of 1 mM and the mixture was cultivated at 28° C. overnight. The cultivated *E. coli* was centrifuged at 8000×g, 4° C. for 30 minutes and the supernatant of the culture solution was collected. Ammonium sulfate was added to the obtained culture solution in an amount of 60% by weight and the proteins were precipitated by salting out. After the salted out solution was left standstill at 4° C. overnight, sediments were collected by centrifuging the solution at 8000×g, 4° C. for 30 min. The obtained sediments were dissolved in 20 mM Tris.HCl/500 mM NaCl buffer, and 1 L of the buffer was dialyzed. The protein solution after the dialysis was added to a column filled with His.Bind® and Resin (Novagen Corporation) and purified by metal chelate affinity chromatography with Ni ion. It was confirmed that the purified hu4D5-8 scFv with an purified N terminus peptide and an MMP-2 substrate introduced at the N terminus (scFv-NPM) showed a single band and had a molecular weight of about 28 kDa in SDS-PAGE.

The prepared scFv-NPM had the following sequence.

(SEQ ID NO. 7)
MSGGGSGGGSGPLGVRGAMDIQMTQSPSSLSASVGDRVTITCRASQDVNT

AVAWYQQKPGKAPKLLIYSASFLYSGVPSRFSGSRSGTDFTLTISSLQPE

DFATYYCQQHYTTPPTFGQGTKVEIKGGGGSGGGGSGGGGSEVQLVESGG

GLVQPGGSLRLSCAASGFNIKDTYIHWVRQAPGKGLEWVARIYPTNGYTR

YADSVKGRFTISADTSKNTAYLQMNSLRAEDTAVYYCSRWGGDGFYAMDY

WGQGTLVTVSSAAALEHHHHHHGGC

Example 10

Confirmation of Cleavage of scFv-NPM at the Linker Moiety by the Addition of MMP-2

Figure 8:
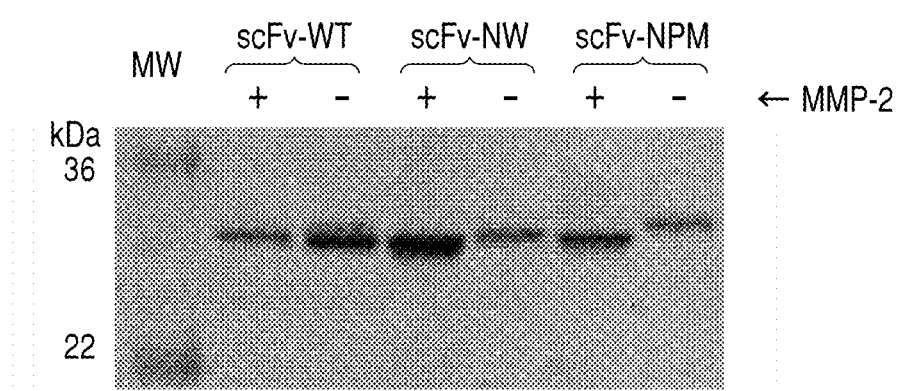
FIG. 8 illustrates the results of reduced type SDS-PAGE of prepared scFv-WT, scFv-NM and scFv-NPM with and without addition of MMP-2.

Change in the molecular weight resulted from the cleavage of the peptide by the addition of MMP-2 to the scFv-NPM prepared above was measured. 0.10 mg/ml of an active type MMP-2 was added in about 10 nM to about 4 µM of PEGylated scFv dialyzed in a TCNB buffer, and the reaction was performed for about 20 hours and the change in the molecular weight was measured by reduced type SDS-PAGE. As a result, decrease in the molecular weight was detected in scFv-NPM by adding MMP-2 as shown in FIG. 8. scFv-NM and scFv-CM are also shown for comparison. On the other hand, decrease in the molecular weight was not detected in scFv-WT. It was confirmed from the above that the peptide of scFv-NPM was cleaved by MMP-2.

Example 11

Confirmation of the Change in the Binding Ability of scFv by the Addition of MMP-2

Figure 9:
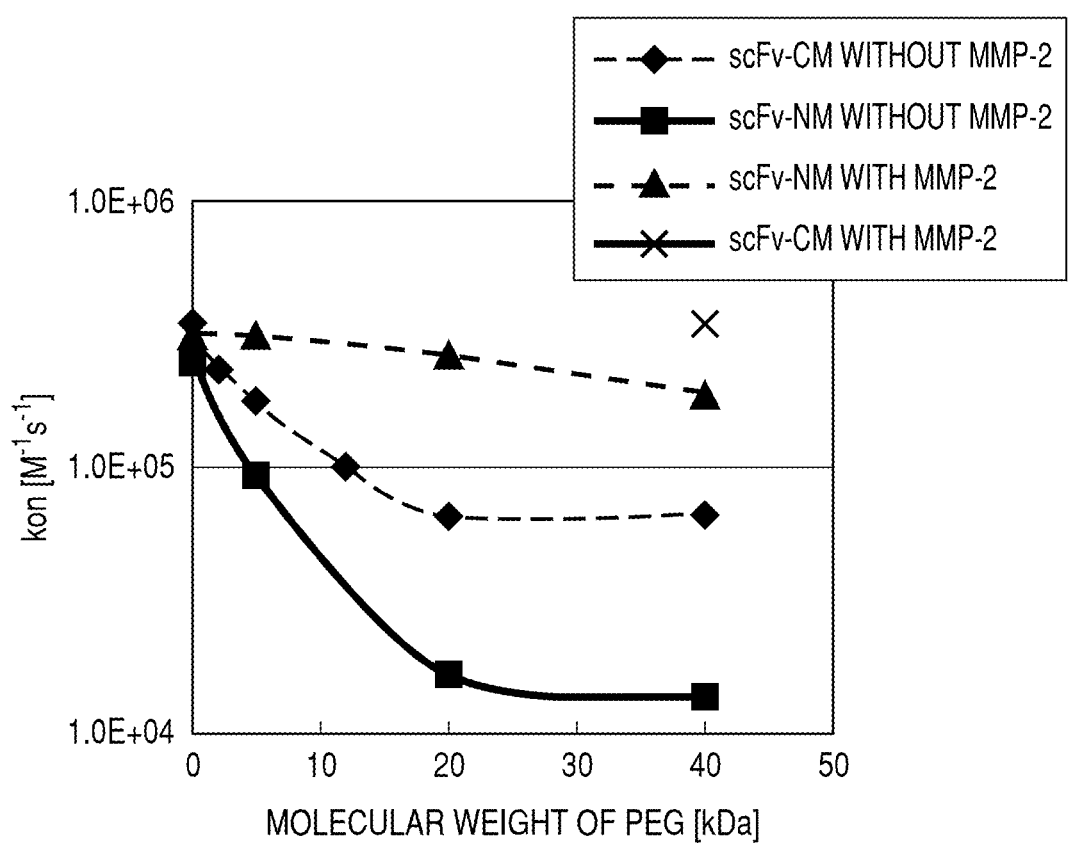
FIG. 9 illustrates the results of the measurement of interaction with HER2 of the prepared N-terminally PEGylated scFv-NM and C-terminally PEGylated scFv-CM PEG with and without addition of MMP-2 using a Biacore X system.

The interaction of various scFv prepared above with HER2, which was an antigen, was measured using Biacore X system (GE Healthcare Co., Ltd.) and the change in the binding ability of various scFv before and after 20 hours of the addition of MMP-2 was measured. As an antigen, Recombinant Human ErbB2/Fc Chimera (with R & D Systems, Inc.) was used for immobilization to the carboxymethyldextran chain on the surface of CM-5 chip by amine coupling according to the recommendation of the manufacture. The immobilized amount was about 1000 to 1300 RU. As a running buffer, PBS-T (2.68 mM KCl/137 mM NaCl/1.47 mM $KH_2PO_4$/1 mM $Na_2HPO_4$/0.005% Tween 20, pH 7.4) was used and samples prepared in 5 to 100 nM were injected under a condition of 20 μL/min in the flow rate, and the binding ability was evaluated. The binding ability were evaluated for scFv-CM without the addition of MMP-2, samples in which PEG-maleimide of 2, 5, 12, 20 or 40 kDa was introduced to the C terminus of scFv-CM without the addition of MMP-2, a samples in which PEG-maleimide of 40 kDa was introduced to the C terminus of scFv-CM after the addition of MMP-2, scFv-NM with or without the addition of MMP-2, scFv-NPM with or without the addition of MMP-2, samples in which PEG-aldehyde of 5, 20 or 40 kDa was introduced to the N terminus of scFv-NM with or without the addition of MMP-2, as the samples whose binding ability was evaluated. In FIG. 9, the results of interaction with HER2 measured for N-terminally PEGylated scFv-NM, C-terminally PEGylated scFv-CM prepared with or without the addition of MMP-2 using the Biacore X system are shown by logarithm of the obtained association rate constant (kon) in the vertical axis and molecular weight of PEG in the horizontal axis. As shown in FIG. 9, It was confirmed that introduction of PEG to the N terminus was able to reduce kon more significantly than the introduction to the C terminus and that kon was able to be changed by the addition of MMP-2. Specifically, scFv-NM in which 5 kDa PEG was introduced to the N terminus showed a value of kon comparable to scFv-CM in which 12 kDa PEG was introduced to the C terminus, and thus it was confirmed that kon was able to be decreased more significantly with a low molecular weight PEG in the N terminus than in the C terminus. In addition, the degree of change in kon by the addition of MMP-2 is about 5 times in scFv-CM in which 40 kDa PEG was introduced to the C terminus while the value is about 15 times in scFv-NM in which 20 kDa PEG was introduced to the N terminus, and thus it was confirmed that the binding ability was able to be changed more significantly in the N terminus than in the C terminus. Furthermore, it was confirmed that the change in kon was comparable when the change in kon for scFv-NM and scFv-NPM before and after the addition of MMP-2 was compared.

Example 12

Preparation of Conjugates of scFv-NM with PEGylated N Terminus and Iron Oxide Particles The scFv-NM with PEGylated N terminus having 5 kDa, 20 kDa or 40 kDa PEG which were prepared in example 4 were reduced in 100 mM phosphate buffer (pH 7.4) at 25° C. for 2 hours under existence of TCEP in 10-timie molar amount. The reduced scFv-NM with PEGylated N terminus was reacted with iron oxide particles containing PEG300 (nanomag-D-SPIO manufactured by Corefront Corporation) of which surface is modified with maleimide group in 1/2000-timie molar amount at 4° C. overnight. After the reaction, scFv-NM with PEGylated N terminus which was not bound to the particles was removed by ultrafiltration using Amicon Ultra-4 (Millipore Corporation) of which pore size was 100 kDa. L-cysteine was added to the filtrated product at 1 mM as the final concentration to block non-reacted maleimide group on the particles. Conjugates of scFv-NM with PEGylated N terminus and iron oxide particles were obtained by removing non-reacted L-cysteine by gel filtration using PD-10 column (GE Healthcare).

Average hydrodynamic diameters of the obtained conjugates of scFv-NM with PEGylated N terminus and iron oxide particles having 5 kDa, 20 kDa or 40 kDa PEG were determined to be 185, 188 and 192 nm respectively by dynamic light scattering techniques. On the other hand, average hydrodynamic diameter of iron oxide particles reacted with L-cysteine was about 174 nm, which was smaller than the conjugates. Therefore, it was confirmed that scFv-NM with PEGylated N terminus was immobilized on the iron oxide particle and that conjugates of scFv-NM with PEGylated N terminus and iron oxide particles were obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-152611, filed Jun. 26, 2009, and Japanese Patent Application No. 2010-109288, filed May 11, 2010 which are hereby incorporated by reference herein in their entirety.

What is claimed is:

1. A compound represented by general formula (1-1):

L-Y-A  (1-1)

wherein, A is a single-chain antibody moiety, which is a polypeptide comprising an antigen-binding site; L is a linker moiety, which is a polypeptide comprising a protease cleavage site; Y is a peptide moiety, which comprises 1 or more amino acids connecting the linker moiety L with the single-chain antibody moiety A; and the linker moiety L binds to an N terminus of the peptide moiety Y, and the peptide moiety Y binds to an N terminus of the single-chain antibody moiety A in (1-1), and wherein L-Y-A (1-1) comprises a polypeptide comprising either one of the amino acid sequences of SEQ ID NO: 4 and SEQ ID NO: 7.

2. A compound represented by general formula (2-1):

X-L-Y-A  (2-1)

wherein, A is a single-chain antibody moiety, which is a polypeptide comprising an antigen-binding site; L is a linker moiety, which is a polypeptide comprising a protease cleavage site; Y is a peptide moiety, which comprises 1 or more amino acids connecting the linker moiety L with the single-chain antibody moiety A;

the linker moiety L binds to an N terminus of the peptide moiety Y, and the peptide moiety Y binds to an N terminus of the single-chain antibody moiety A in (2-1); and X is either one of polyethylene glycol, an organic dye, an organic polymer and a particle and binds to the linker moiety in (2-1), and wherein X-L-Y-A (2-1) comprises a polypeptide comprising either one of the amino acid sequences of SEQ ID NO: 4 and SEQ ID NO: 7.

3. The compound according to claim 2, wherein the molecular weight of the polyethylene glycol is not less than 20 kDa and not more than 40 kDa.

4. The compound according to claim 1, wherein the single-chain antibody moiety is further bound to signal generating molecules selected from the group consisting of radionuclides, molecules which emit MRI signals, molecules which emit supersonic wave signals and molecules which emit fluorescence signals.

5. The compound according to claim 1, wherein the single-chain antibody moiety is further bound to iron oxide particles.

6. The compound according to claim 2, wherein the single-chain antibody moiety is bound to signal generating molecules selected from the group consisting of radionuclides, molecules which emit MRI signals, molecules which emit supersonic wave signals and molecules which emit fluorescence signals.

7. The compound according to claim 2, wherein the single-chain antibody moiety is further bound to iron oxide particles.

8. The compound according to claim 1 of which a cleaved product of the compound at the protease cleavage site has higher antigen binding ability than the compound before cleavage.

9. The compound according to claim 2 of which a cleaved product of the compound at the protease cleavage site has higher antigen binding ability than the compound before cleavage.

* * * * *